(12) United States Patent
Crall et al.

(10) Patent No.: US 8,636,783 B2
(45) Date of Patent: Jan. 28, 2014

(54) SPINAL STABILIZATION SYSTEMS AND METHODS

(75) Inventors: Angela Crall, Austin, TX (US); Kameron Scott Ely, Cedar Park, TX (US); Bruce A. Riceman, Leander, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 681 days.

(21) Appl. No.: 12/186,446

(22) Filed: Aug. 5, 2008

(65) Prior Publication Data

US 2008/0288002 A1 Nov. 20, 2008

Related U.S. Application Data

(63) Continuation-in-part of application No. 11/959,063, filed on Dec. 18, 2007.

(60) Provisional application No. 60/882,818, filed on Dec. 29, 2006.

(51) Int. Cl.
*A61B 17/04* (2006.01)

(52) U.S. Cl.
USPC .......................................... 606/308; 606/272

(58) Field of Classification Search
USPC ......... 606/246, 248, 266, 267, 268, 269, 300, 606/301, 305, 308, 272, 319, 257, 265, 307, 606/302, 306, 320, 328
See application file for complete search history.

(56) References Cited

U.S. PATENT DOCUMENTS

| 4,763,644 A | 8/1988 | Webb |
| 5,042,982 A | 8/1991 | Harms et al. |
| 5,067,955 A | 11/1991 | Cotrel |

(Continued)

FOREIGN PATENT DOCUMENTS

| DE | 86 13 638 | 10/1986 |
| DE | 88 04 457 U1 | 7/1988 |

(Continued)

OTHER PUBLICATIONS

International Search Report and Written Opinion for PCT/US2007/086322, dated May 8, 2008, 15 pages.

(Continued)

*Primary Examiner* — Eduardo C Robert
*Assistant Examiner* — Atiya Mahmud
(74) *Attorney, Agent, or Firm* — Seager, Tufte & Wickhem, LLC

(57) ABSTRACT

One embodiment provides a bone fastener including a collar, a fastener member, and a pin. The collar can have an upper portion with slot to receive an elongated member and a lower portion with a socket and an opening. The fastener member can have head and shank portions. The socket can receive the head portion and prevent movement of the head portion through the opening when the head portion is out of registration with the opening. The head portion and the socket can be configured to allow angulation of the fastener member within a defined range of motion within a selected plane. The head portion and the socket can define apertures which can be aligned with each other when the head portion is in the socket and which can receive the pin. One embodiment provides a generally spherical head portion with a flat.

2 Claims, 12 Drawing Sheets

Step 1: Align Screw with Tulip

(56) References Cited

U.S. PATENT DOCUMENTS

| | | |
|---|---|---|
| 5,129,388 A | 7/1992 | Vignaud et al. |
| 5,154,719 A | 10/1992 | Cotrel |
| 5,176,680 A | 1/1993 | Vignaud et al. |
| 5,217,497 A | 6/1993 | Mehdian |
| 5,226,766 A | 7/1993 | Lasner |
| 5,261,912 A | 11/1993 | Frigg |
| 5,261,913 A | 11/1993 | Marnay |
| 5,346,493 A | 9/1994 | Stahurski et al. |
| 5,385,583 A | 1/1995 | Cotrel |
| 5,397,363 A | 3/1995 | Gelbard |
| 5,417,533 A | 5/1995 | Lasner |
| 5,486,174 A | 1/1996 | Fournet-Fayard et al. |
| 5,520,689 A | 5/1996 | Schlapfer et al. |
| 5,545,165 A | 8/1996 | Biedermann et al. |
| 5,562,663 A | 10/1996 | Wisnewski et al. |
| 5,591,165 A | 1/1997 | Jackson |
| 5,611,800 A | 3/1997 | Davis et al. |
| 5,613,968 A | 3/1997 | Lin |
| 5,634,925 A | 6/1997 | Urbanski |
| 5,643,261 A | 7/1997 | Schafer |
| 5,643,264 A | 7/1997 | Sherman |
| 5,662,653 A | 9/1997 | Songer et al. |
| 5,683,390 A | 11/1997 | Metz-Stavenhagen et al. |
| 5,697,929 A | 12/1997 | Mellinger |
| 5,725,527 A | 3/1998 | Biedermann et al. |
| 5,728,098 A | 3/1998 | Sherman et al. |
| 5,738,685 A | 4/1998 | Halm et al. |
| 5,752,957 A | 5/1998 | Ralph et al. |
| 5,797,911 A | 8/1998 | Sherman et al. |
| 5,863,293 A | 1/1999 | Richelsoph |
| 5,879,350 A | 3/1999 | Sherman et al. |
| 5,947,967 A | 9/1999 | Barker |
| 5,964,760 A | 10/1999 | Richelsoph |
| 5,989,250 A | 11/1999 | Wagner et al. |
| 5,989,254 A * | 11/1999 | Katz ............................ 606/308 |
| 6,016,727 A | 1/2000 | Morgan |
| 6,063,090 A | 5/2000 | Schlapfer et al. |
| 6,074,391 A | 6/2000 | Metz-Stavenhagen et al. |
| 6,077,262 A | 6/2000 | Schlapfer |
| 6,083,227 A | 7/2000 | Saurat et al. |
| 6,117,137 A | 9/2000 | Halm et al. |
| 6,132,430 A | 10/2000 | Wagner |
| 6,183,473 B1 | 2/2001 | Ashman |
| 6,193,719 B1 | 2/2001 | Gournay et al. |
| 6,224,596 B1 | 5/2001 | Jackson |
| 6,248,105 B1 | 6/2001 | Schlapfer et al. |
| 6,280,442 B1 | 8/2001 | Barker et al. |
| 6,287,308 B1 | 9/2001 | Betz et al. |
| 6,290,700 B1 | 9/2001 | Schmotzer |
| 6,302,888 B1 | 10/2001 | Mellinger et al. |
| 6,325,802 B1 | 12/2001 | Frigg |
| 6,413,257 B1 | 7/2002 | Lin et al. |
| 6,458,132 B2 | 10/2002 | Choi |
| 6,478,797 B1 | 11/2002 | Paul |
| 6,485,494 B1 | 11/2002 | Haider |
| 6,520,963 B1 | 2/2003 | McKinley |
| 6,540,748 B2 | 4/2003 | Lombardo |
| 6,540,749 B2 | 4/2003 | Schafer et al. |
| 6,551,318 B1 | 4/2003 | Stahurski |
| 6,554,834 B1 | 4/2003 | Crozet et al. |
| 6,562,040 B1 | 5/2003 | Wagner |
| 6,565,565 B1 | 5/2003 | Yuan et al. |
| 6,613,050 B1 | 9/2003 | Wagner et al. |
| 6,648,887 B2 | 11/2003 | Ashman |
| 6,660,005 B2 | 12/2003 | Toyama et al. |
| 6,673,074 B2 | 1/2004 | Shluzas |
| 6,706,045 B2 | 3/2004 | Lin et al. |
| 6,716,214 B1 | 4/2004 | Jackson |
| 6,730,093 B2 | 5/2004 | Saint Martin |
| 6,736,820 B2 | 5/2004 | Biedermann et al. |
| 6,740,089 B2 | 5/2004 | Haider |
| 6,783,527 B2 | 8/2004 | Drewry et al. |
| 6,835,196 B2 | 12/2004 | Biedermann et al. |
| 6,858,030 B2 | 2/2005 | Martin et al. |
| 6,918,911 B2 | 7/2005 | Biedermann et al. |
| 6,974,460 B2 | 12/2005 | Carbone et al. |
| 6,981,973 B2 | 1/2006 | McKinley |
| 7,018,378 B2 | 3/2006 | Biedermann et al. |
| 7,066,937 B2 | 6/2006 | Shluzas |
| 7,094,237 B2 | 8/2006 | Gradel et al. |
| 7,156,850 B2 | 1/2007 | Kim |
| 7,223,268 B2 | 5/2007 | Biedermann |
| 7,235,075 B1 | 6/2007 | Metz-Stavenhagen |
| 7,264,621 B2 | 9/2007 | Coates et al. |
| 7,320,556 B2 | 1/2008 | Vagn-Erik |
| 7,377,923 B2 | 5/2008 | Purcell et al. |
| 7,678,137 B2 | 3/2010 | Butler et al. |
| 7,749,258 B2 | 7/2010 | Biedermann et al. |
| 7,947,065 B2 | 5/2011 | Hammill, Sr. et al. |
| 2001/0023350 A1 | 9/2001 | Choi |
| 2002/0138076 A1 | 9/2002 | Biedermann et al. |
| 2003/0100904 A1 | 5/2003 | Biedermann |
| 2003/0125742 A1 | 7/2003 | Yuan et al. |
| 2004/0138662 A1 | 7/2004 | Landry et al. |
| 2004/0162560 A1 | 8/2004 | Raynor et al. |
| 2004/0181224 A1 | 9/2004 | Biedermann et al. |
| 2004/0230192 A1* | 11/2004 | Graf ............................... 606/61 |
| 2004/0236330 A1* | 11/2004 | Purcell et al. ................... 606/61 |
| 2004/0260283 A1 | 12/2004 | Wu et al. |
| 2005/0049589 A1* | 3/2005 | Jackson ........................... 606/61 |
| 2005/0059973 A1 | 3/2005 | Dierks |
| 2005/0080420 A1 | 4/2005 | Farris et al. |
| 2005/0096659 A1 | 5/2005 | Freudiger |
| 2005/0137594 A1 | 6/2005 | Doubler et al. |
| 2005/0154391 A1 | 7/2005 | Doherty et al. |
| 2005/0159750 A1 | 7/2005 | Doherty |
| 2005/0187548 A1 | 8/2005 | Butler et al. |
| 2005/0203515 A1 | 9/2005 | Doherty et al. |
| 2005/0228379 A1 | 10/2005 | Jackson |
| 2005/0277927 A1 | 12/2005 | Guenther et al. |
| 2005/0283157 A1 | 12/2005 | Coates et al. |
| 2006/0025768 A1 | 2/2006 | Iott et al. |
| 2006/0074419 A1 | 4/2006 | Taylor et al. |
| 2006/0084979 A1 | 4/2006 | Jackson |
| 2006/0089644 A1* | 4/2006 | Felix ............................... 606/61 |
| 2006/0111715 A1* | 5/2006 | Jackson ........................... 606/61 |
| 2006/0142761 A1* | 6/2006 | Landry et al. .................. 606/61 |
| 2006/0149232 A1 | 7/2006 | Sasing |
| 2006/0149240 A1 | 7/2006 | Jackson |
| 2006/0161152 A1 | 7/2006 | Ensign et al. |
| 2006/0173456 A1 | 8/2006 | Hawkes et al. |
| 2006/0217716 A1 | 9/2006 | Baker et al. |
| 2006/0217717 A1 | 9/2006 | Whipple |
| 2006/0235385 A1 | 10/2006 | Whipple |
| 2006/0235389 A1* | 10/2006 | Albert et al. ..................... 606/61 |
| 2006/0235392 A1 | 10/2006 | Hammer et al. |
| 2006/0241594 A1 | 10/2006 | McCarthy et al. |
| 2006/0241603 A1 | 10/2006 | Jackson |
| 2007/0043355 A1* | 2/2007 | Bette et al. ..................... 606/61 |
| 2007/0055257 A1 | 3/2007 | Vaccaro et al. |
| 2007/0083199 A1 | 4/2007 | Baccelli |
| 2007/0093820 A1 | 4/2007 | Freudiger |
| 2007/0118118 A1 | 5/2007 | Kwak et al. |
| 2007/0118123 A1 | 5/2007 | Strausbaugh et al. |
| 2007/0161994 A1 | 7/2007 | Lowery et al. |
| 2007/0161996 A1* | 7/2007 | Biedermann et al. ........... 606/61 |
| 2007/0173833 A1 | 7/2007 | Butler et al. |
| 2007/0191835 A1* | 8/2007 | Justis et al. ..................... 606/61 |
| 2007/0233071 A1 | 10/2007 | Dewey et al. |
| 2007/0233086 A1 | 10/2007 | Harms et al. |
| 2007/0260246 A1 | 11/2007 | Biedermann |
| 2008/0015586 A1 | 1/2008 | Krishna et al. |
| 2008/0114362 A1* | 5/2008 | Justis et al. ..................... 606/72 |
| 2008/0147129 A1* | 6/2008 | Biedermann et al. ......... 606/308 |
| 2008/0161859 A1* | 7/2008 | Nilsson ......................... 606/266 |
| 2008/0177321 A1* | 7/2008 | Drewry et al. ................. 606/266 |
| 2008/0234759 A1* | 9/2008 | Marino ......................... 606/309 |
| 2008/0269809 A1 | 10/2008 | Garamszegi |
| 2010/0145394 A1 | 6/2010 | Harvey et al. |
| 2010/0160977 A1 | 6/2010 | Gephart et al. |
| 2010/0204735 A1 | 8/2010 | Gephart et al. |
| 2011/0118793 A1 | 5/2011 | Shluzas |

(56) References Cited

U.S. PATENT DOCUMENTS

FOREIGN PATENT DOCUMENTS

| | | |
|---|---|---|
| DE | 41 10 002 C1 | 5/1992 |
| DE | 196 46 534 A1 | 5/1998 |
| DE | 198 26 380 A1 | 12/1999 |
| DE | 100 04 444 A1 | 8/2001 |
| DE | 198 26 380 B4 | 9/2005 |
| DE | 10 2005 005 647 A1 | 8/2006 |
| DE | 195 34 136 A1 | 12/2007 |
| EP | 0 487 895 B1 | 1/1995 |
| EP | 0 616 512 B1 | 8/1997 |
| EP | 0 773 746 B1 | 9/1999 |
| EP | 0 672 388 B1 | 12/1999 |
| EP | 1 335 676 B1 | 8/2003 |
| EP | 1335675 B1 | 1/2005 |
| EP | 1 210 914 B1 | 5/2005 |
| EP | 1 316 295 B1 | 10/2005 |
| EP | 1 050 276 B1 | 12/2005 |
| EP | 1 294 296 B1 | 1/2007 |
| FR | 2 789 293 A1 | 8/2000 |
| FR | 2 896 981 A1 | 8/2007 |
| JP | 10-33552 A | 2/1998 |
| JP | 2001-276086 A | 10/2001 |
| WO | WO 94/08527 A1 | 4/1994 |
| WO | WO 94/11642 A1 | 5/1994 |
| WO | WO 95/13756 A1 | 5/1995 |
| WO | WO 96/39972 A1 | 12/1996 |
| WO | WO 98/31293 A1 | 7/1998 |
| WO | WO 99/56652 A1 | 11/1999 |
| WO | WO 00/62691 A1 | 10/2000 |
| WO | WO 02/00125 A1 | 1/2002 |
| WO | WO 02/02024 A1 | 1/2002 |
| WO | WO 02/069854 A1 | 9/2002 |
| WO | WO 02/094114 A1 | 11/2002 |
| WO | WO 03/003901 A2 | 1/2003 |
| WO | WO 03/003902 A2 | 1/2003 |
| WO | WO 03/061494 A1 | 7/2003 |
| WO | WO 03/068086 A1 | 8/2003 |
| WO | WO 03/075811 A1 | 9/2003 |
| WO | WO 03/096916 A1 | 11/2003 |
| WO | WO 2004/091413 A1 | 10/2004 |
| WO | WO 2004/103194 A1 | 12/2004 |
| WO | WO 2006/070961 A2 | 7/2006 |
| WO | WO 2006/084443 A1 | 8/2006 |
| WO | WO 2006/104538 A1 | 10/2006 |
| WO | WO 2006/104709 A2 | 10/2006 |
| WO | WO 2006/110463 A1 | 10/2006 |
| WO | WO 2007/041265 A1 | 4/2007 |
| WO | WO 2007/045895 A1 | 4/2007 |
| WO | WO 2007/050373 A2 | 5/2007 |
| WO | WO 2007/087486 A1 | 8/2007 |
| WO | WO 2007/100953 A1 | 9/2007 |
| WO | WO 2007/101267 A1 | 9/2007 |
| WO | WO 2007/127682 A1 | 11/2007 |

OTHER PUBLICATIONS

International Preliminary Report on Patentability, PCT/US2007/086322, issued Jun. 30, 2009, 8 pages.

Office Action issued in U.S. Appl. No. 11/959,063 mailed Jun. 10, 2011, 16 pages.

Office Action for U.S. Appl. No. 11/959,063 mailed Nov. 22, 2011, 19 pgs.

\* cited by examiner

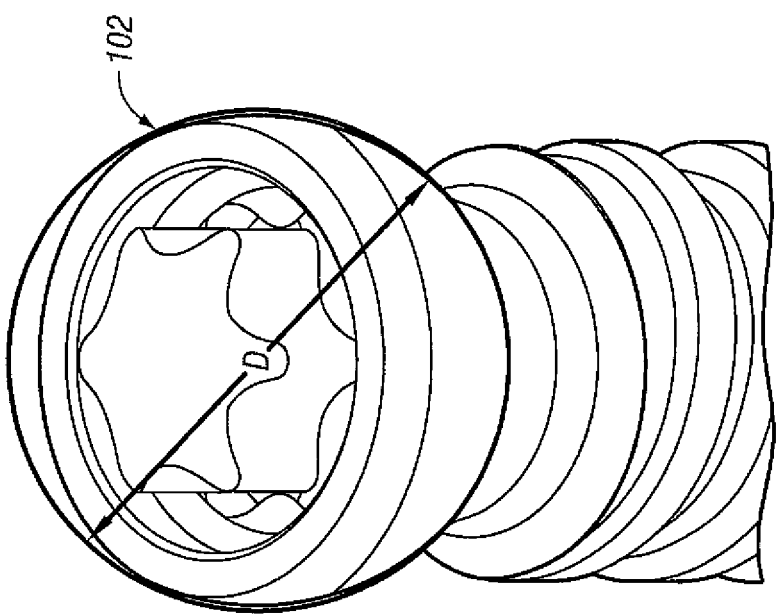
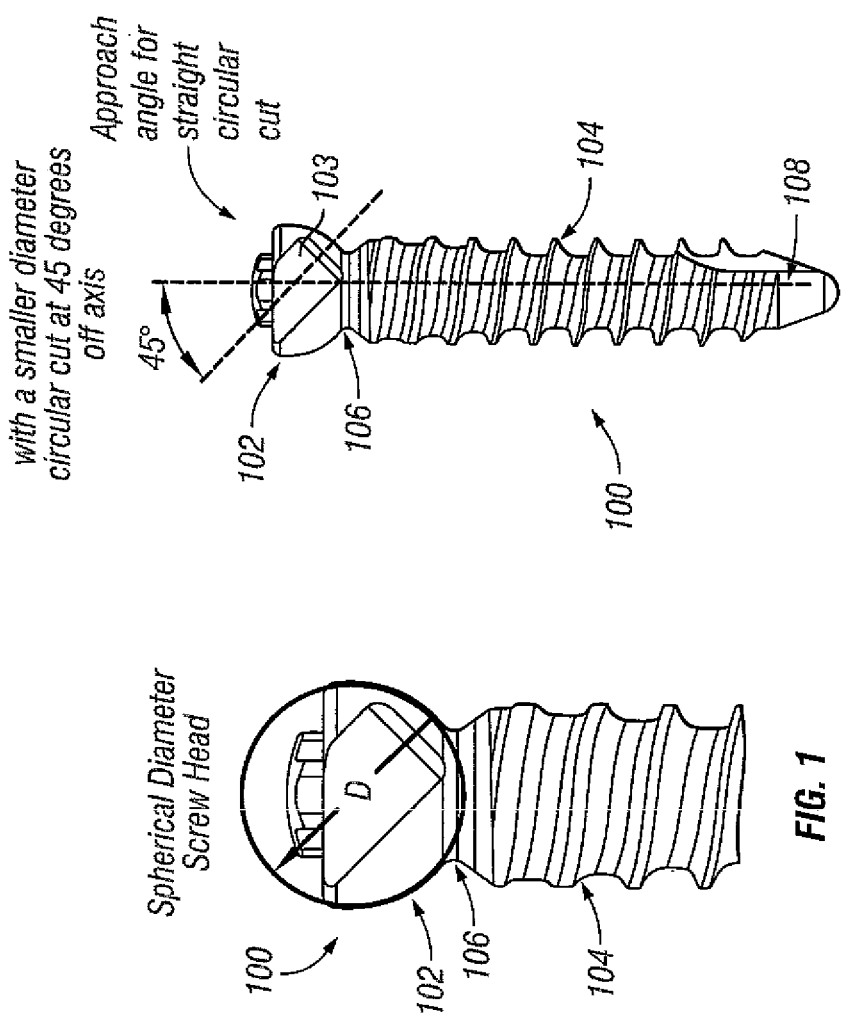

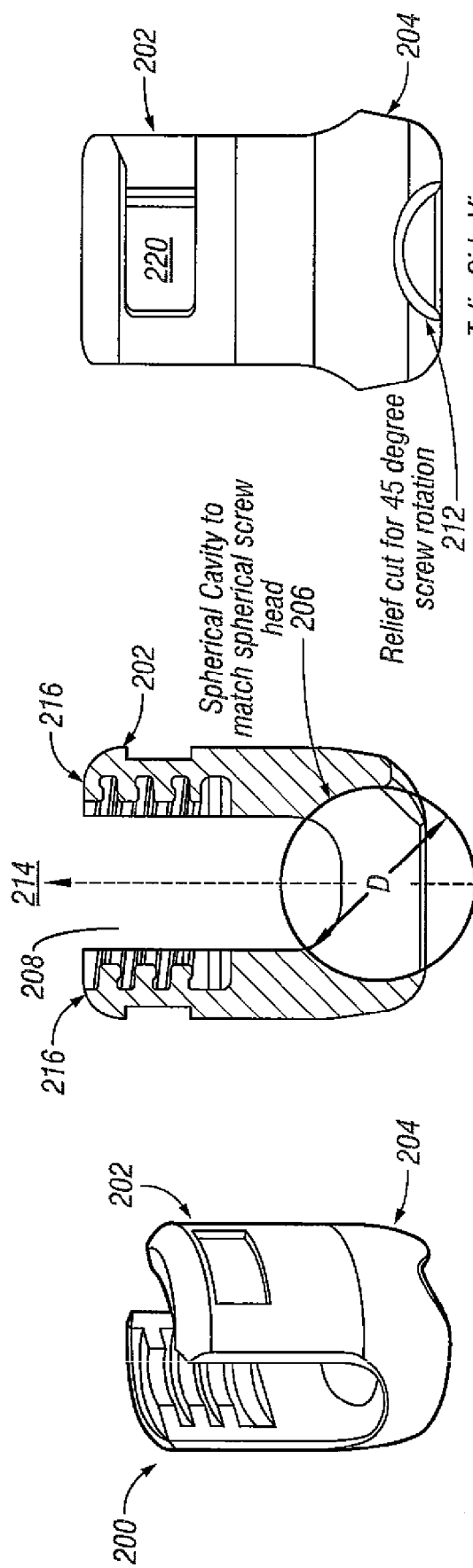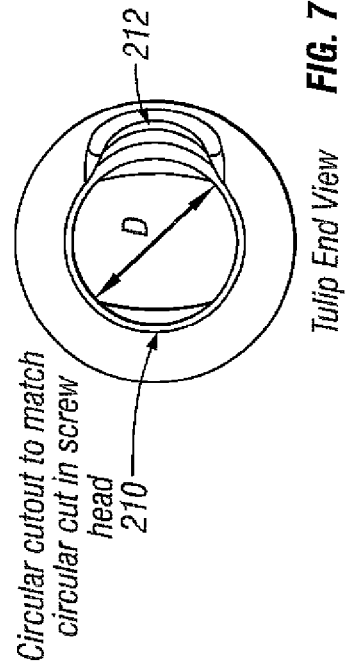

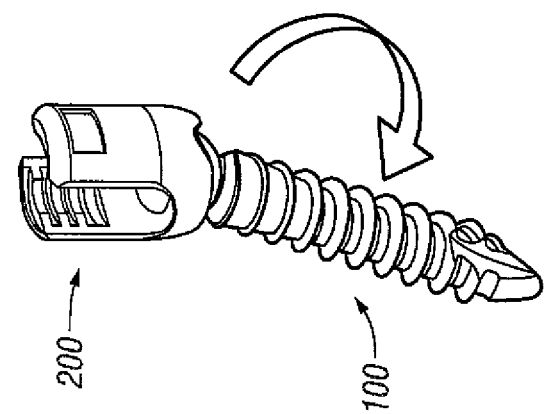
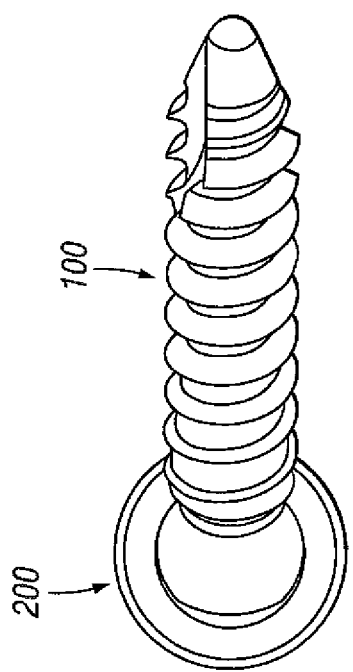
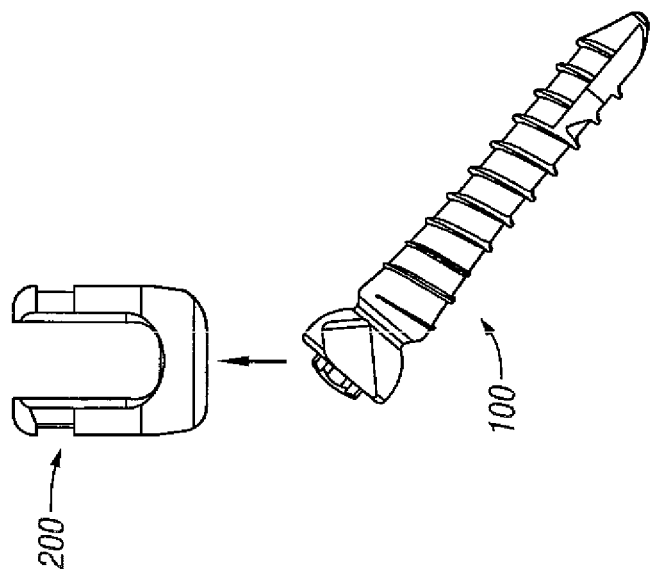

SECTION C-C

SELF TAPPING 108

5° CONICAL 104
102
45°

108
104
102
110
VIEW B-B (60°)

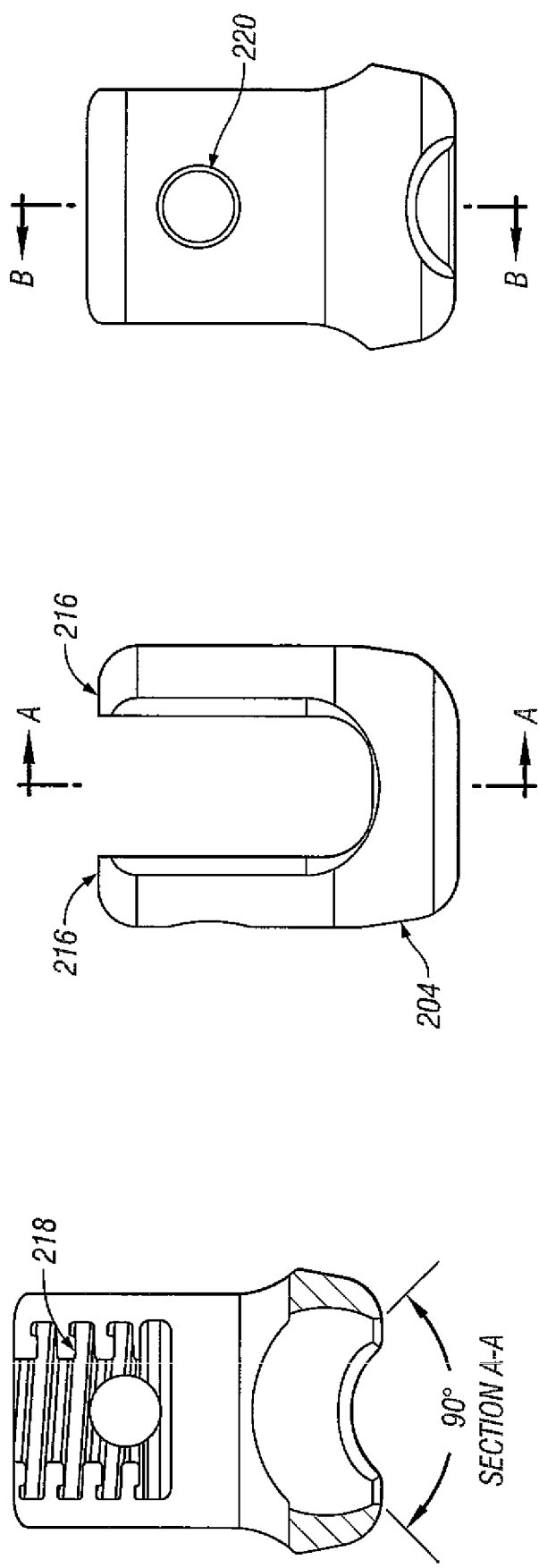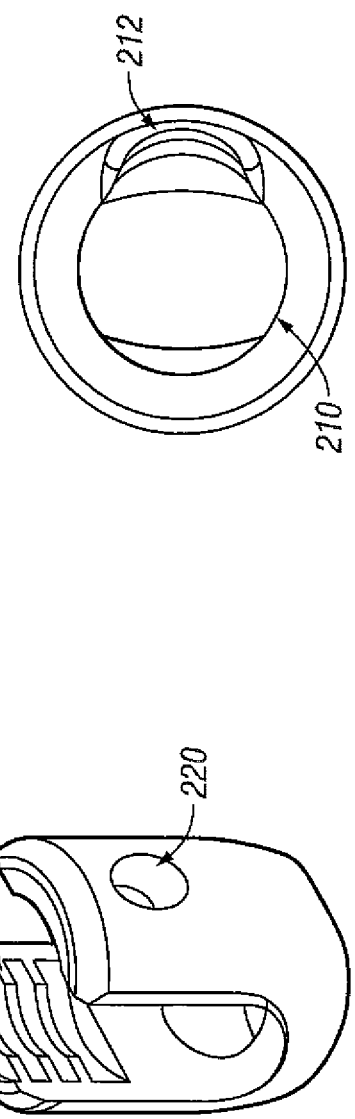

SPINAL STABILIZATION SYSTEMS AND METHODS

CROSS-REFERENCE TO RELATED APPLICATIONS

This application is a continuation-in-part of U.S. patent application Ser. No. 11/959,063, filed Dec. 18, 2007, entitled "SPINAL STABILIZATION SYSTEMS AND METHODS," which claims priority from provisional patent application No. 60/882,818, filed Dec. 29, 2006, entitled "SPINAL STABILIZATION SYSTEMS AND METHODS," both of which are hereby fully incorporated herein for all purposes.

BACKGROUND OF THE INVENTION

1. Field of the Invention

The present invention generally relates to a polyaxial fastener assembly, and spinal stabilization systems that include at least one polyaxial fastener. Embodiments of the invention relate to spinal stabilization systems that can be inserted into a patient preferrably using a minimally invasive surgical procedure. More particularly, embodiments disclosed herein relate to monoaxial fastener assembly created from a polyaxial fastener assembly. Embodiments of the invention relate to methods of assembling implant system components, methods of assembling stabilization systems and components, as well as the methods and tools employed for performing minimally invasive spinal stabilization procedures.

2. Description of Related Art

Bone can be subject to degeneration caused by trauma, disease, and/or aging. Degeneration can destabilize bone and affect surrounding structures. For example, destabilization of a spine can result in alteration of a natural spacing between adjacent vertebrae. Alteration of a natural spacing between adjacent vertebrae can subject nerves that pass between vertebral bodies to pressure. Pressure applied to the nerves can cause pain and/or nerve damage. Maintaining the natural spacing between vertebrae can reduce pressure applied to nerves that pass between vertebral bodies. A spinal stabilization procedure can be used to maintain the natural spacing between vertebrae and promote spinal stability.

Spinal stabilization can involve accessing a portion of the spine through soft tissue. Conventional stabilization systems can require a large incision and/or multiple incisions in the soft tissue to provide access to a portion of the spine to be stabilized. Conventional procedures can result in trauma to the soft tissue, for example, due to muscle stripping.

Spinal stabilization systems for a lumbar region of the spine can be inserted during a spinal stabilization procedure using a posterior spinal approach. Conventional systems and methods for posterolateral spinal fusion can involve dissecting and retracting soft tissue proximate the surgical site. Dissection and retraction of soft tissue can cause trauma to the soft tissue, and extend recovery time. Minimally invasive procedures and systems can reduce recovery time as well as trauma to the soft tissue surrounding a stabilization site.

U.S. Pat. No. 6,530,929 to Justis et al. (hereinafter "Justis"), which is incorporated by reference as if fully disclosed herein, describes minimally invasive techniques and instruments for stabilizing a bony structure in an animal subject. Justis provides a method for using an instrument to connect at least two bone anchors with a connecting element. The instrument is secured to the anchors and manipulated to place the connecting element in a position more proximate the anchors.

U.S. Patent Application Publication No. 20060084993, which is incorporated by reference as if fully disclosed herein, describes a spinal stabilization system including bone fastener assemblies having a bone fastener and a collar. The collar can be rotated and/or angulated relative to the bone fastener. Detachable members can be coupled to the collar to allow for formation of the spinal stabilization system through a small skin incision. The detachable members can allow for alignment of the collars to facilitate insertion of an elongated member in the collars.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention includes a spinal stabilization system to be installed in a patient to stabilize a portion of a spine. The spinal stabilization system can be installed using a minimally invasive procedure. An instrumentation kit can provide instruments and spinal stabilization system components necessary for forming a spinal stabilization system in a patient.

The invention also includes a spinal stabilization system that can be used to achieve rigid pedicle fixation while minimizing the amount of damage to surrounding tissue. In some embodiments, a spinal stabilization system can be used to provide stability to two or more vertebrae. A spinal stabilization system can include an elongated member, two or more bone fastener assemblies, and/or a closure member. The bone fastener assembly can include, but is not limited to, a bone fastener and a collar (or tulip). A first portion of the bone fastener can couple to a portion of the spine during use. A first portion of a collar (or tulip) includes a socket which can couple to a second portion of the bone fastener. A second portion of the collar can couple to an elongated member during use. In some embodiments, an orientation of the bone fastener can be independent of the orientation of the collar for a bone fastener assembly. After the bone fastener is placed in a vertebral body, the collar coupled to the bone fastener can be positioned so that the elongated member can be positioned in the collar and in at least one other collar that is coupled to another vertebral body by a bone fastener.

In accordance with one aspect of the invention, a bone fastener assembly includes a bone fastener, and a collar. The collar has an upper portion with a slot to receive an elongated member, a lower portion having a socket formed therein and an opening with a predetermined shape in communication with the socket, and a first longitudinal axis extending through the upper and lower portions. The bone fastener has a head portion to be received in the socket, and a shank portion to be attached to a vertebrae. The head portion has a first cross-sectional shape in a plane generally perpendicular to a second longitudinal axis extending through the head and shank portions of the fastener. The head portion further includes a second cross-sectional shape in a plane angled relative to the second longitudinal axis. The first cross-sectional shape is configured to prohibit movement of the head portion through the opening in the collar and the second cross-sectional shape is configured to allow movement of the head portion through the opening.

The head is positioned in a socket of the collar through the opening in bottom surface of the collar under a particular orientation with respect to the collar. In a preferred embodiment, the predetermined shape of the opening includes a first portion having a generally circular shape in a plane perpendicular to the first longitudinal axis, and a second portion having a relief extending from the generally circular shape. In this embodiment, and in order to permit insertion of the fastener into the collar, the fastener is oriented such that the second cross-sectional shape of the fastener is keyed to register with the circular shape and relief of the opening.

Further, once the fastener is received within the socket of the collar, separation of the fastener from the collar is inhibited by rotating the fastener to a different orientation with respect to the collar. Indeed, the fastener can be rotated substantially to any angle to reposition the first cross-sectional shape of the head portion out of alignment with the relief. The fastener therefore can be angulated, about a plurality of axes, within the collar (i.e., the bone fastener can move polyaxially relative to the collar within a defined range of motion) without risk of removal from the collar or the socket therein.

In an embodiment, a collar includes, but is not limited to, arms and a body to form a slot to receive an elongated member. When the elongated member is positioned in the collar, a portion of the elongated member can engage or otherwise be coupled to a head of a bone fastener of the bone fastener assembly to lock the position of the various components.

Inner surfaces of the arms of a bone fastener assembly collar can include a thread to engage a complementary thread of a closure member. A closure member secures the elongated member to the bone fastener assembly, and secures the position of the various components. In a preferred embodiment, a modified thread configuration is used.

One embodiment provides a bone fastener including a collar, a fastener member, and a pin. The collar can have an upper portion with slot to receive an elongated member and a lower portion with a socket and an opening. The fastener member can have head and shank portions. The socket can receive the head portion and prevent movement of the head portion through the opening when the head portion is out of registration with the opening. The head portion and the socket can be configured to allow angulation of the fastener member within a defined range of motion within a selected plane. The head portion and the socket can define apertures which can be aligned with each other when the head portion is in the socket and which can receive the pin. One embodiment provides a generally spherical head portion with a flat.

One embodiment provides a method of assembling a bone fastener. The bone fastener can include a fastener member and a collar having a lower portion and an upper portion with a slot formed therein to receive an elongated member. The lower portion of the collar can have a socket formed therein and an opening with a predetermined shape in communication with the socket. A first longitudinal axis can extend through the upper and lower portions of the collar. The fastener member can have a head portion to be received in the socket of the lower portion of the collar. The fastener member can also have a shank portion to be attached to a vertebrae and a second longitudinal axis extending through the head portion and shank portion of the fastener member. The head portion of the fastener member can have a cross-sectional shape in a plane generally perpendicular to the second longitudinal axis.

The method can include aligning the collar with the fastener member with the cross-sectional shape of the head portion registering with the opening. The head portion of the fastener member can be inserted into the socket through the opening in the lower portion of the collar. Movement of the head portion through the opening can be prohibited. The fastener member can be angulated relative to the collar within a defined range of motion within a selected plane defined by the position of the head portion in the socket.

The method can include creating an aperture in the body lower portion of the collar. An aperture can be created in an upper portion of the head portion of the fastener member in a location such that the aperture in the head portion of the fastener member aligns with the aperture in the lower portion of the collar when the head portion of the fastener member is in the socket. In some embodiments, movement of the head portion of the fastener member through the opening in the lower portion of the collar is prevented by inserting a pin coupled to the head portion of the fastener member through an aperture in the lower portion of the collar. Movement of the head portion of the fastener member through the opening in the lower portion of the collar by inserting a pin through apertures in the lower portion of the collar and the head portion of the fastener member.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the method and system of the invention. Together with the written description, the drawings serve to explain the principles of the invention.

BRIEF DESCRIPTION OF THE DRAWINGS

FIG. 1 is an enlarged side view of a representative embodiment of the head portion of the fastener in accordance with the invention.

FIG. 2 is a side view of the complete fastener shown in FIG. 1.

FIG. 3 is an enlarged view of a perspective view of the fastener head portion shown in FIG. 1.

FIG. 4 is a perspective view of a representative embodiment of the collar (or tulip) in accordance with the invention.

FIG. 5 is a cross-sectional view of the collar shown in FIG. 4.

FIG. 6 is a side view of the collar shown in FIG. 4.

FIG. 7 is a bottom view of the collar shown in FIG. 4.

FIGS. 8A-8C depict schematic views of a method of positioning the fastener in the collar in accordance with the invention.

FIG. 13A is another perspective view of a representative embodiment of the collar in accordance with the invention.

FIG. 13B is a front of the collar shown in FIG. 13A.

FIG. 13C is a cross-sectional view taken along line A-A in FIG. 13B.

FIG. 13D is a bottom view of the collar shown in FIG. 13A.

FIG. 13E is a side view of the collar shown in FIG. 13A.

DETAILED DESCRIPTION OF THE PREFERRED EMBODIMENT

Figure 10:
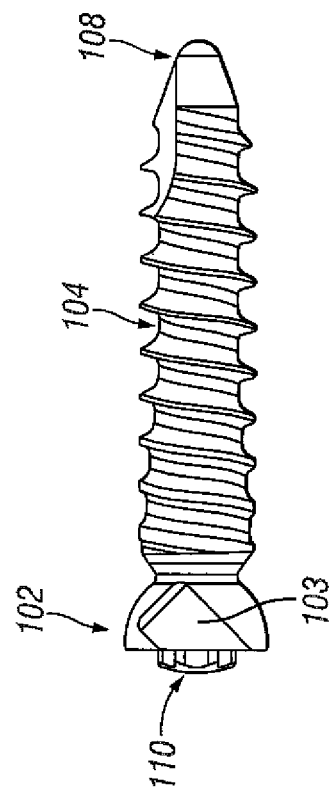
FIG. 10 is a front view of the fastener shown in FIG. 9.
Figure 11:
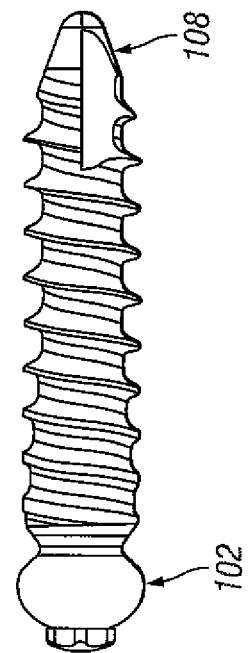
FIG. 11 is a side view of the fastener shown in FIG. 9.

Reference will now be made in detail to the present preferred embodiments of the invention, an example of which is illustrated in the accompanying drawings. The method and corresponding steps of the invention will be described in conjunction with the detailed description of the system.

A spinal stabilization system can be installed in a patient to stabilize a portion of a spine. Spinal stabilization can be used, but is not limited to use, in patients having degenerative disc disease, spinal stenosis, spondylolisthesis, pseudoarthrosis, and/or spinal deformities; in patients having fracture or other vertebral trauma; and in patients after tumor resection. A spinal stabilization system can be installed using a minimally invasive procedure. An instrumentation set can include instruments and spinal stabilization system components for forming a spinal stabilization system in a patient.

A minimally invasive procedure can be used to limit an amount of trauma to soft tissue surrounding vertebrae that are to be stabilized. In some embodiments, the natural flexibility of skin and soft tissue can be used to limit the length and/or depth of an incision or incisions needed during the stabilization procedure. Minimally invasive procedures can provide limited direct visibility in vivo. Forming a spinal stabilization system using a minimally invasive procedure can include using tools to position system components in the body.

A minimally invasive procedure can be performed after installation of one or more spinal implants in a patient. The spinal implant or spinal implants can be inserted using an anterior procedure and/or a lateral procedure. The patient can be turned and a minimally invasive procedure can be used to install a posterior spinal stabilization system. A minimally invasive procedure for stabilizing the spine can be performed without prior insertion of one or more spinal implants in some patients. In some patients, a minimally invasive procedure can be used to install a spinal stabilization system after one or more spinal implants are inserted using a posterior spinal approach.

A spinal stabilization system can be used to achieve rigid pedicle fixation while minimizing the amount of damage to surrounding tissue. In some embodiments, a spinal stabilization system can be used to provide stability to two adjacent vertebrae (i.e., one vertebral level). A spinal stabilization system can include two bone fastener assemblies. One bone fastener assembly can be positioned in each of the vertebrae to be stabilized. An elongated member can be coupled and secured to the bone fastener assemblies. As used herein, "coupled" components can directly contact each other or can be separated by one or more intervening members. In some embodiments, a single spinal stabilization system can be installed in a patient. Such a system can be referred to as a unilateral, single-level stabilization system or a single-level, two-point stabilization system. In some embodiments, two spinal stabilization systems can be installed in a patient on opposite sides of a spine. Such a system can be referred to as a bilateral, single-level stabilization system or a single-level, four-point stabilization system.

In some embodiments, a spinal stabilization system can provide stability to three or more vertebrae (i.e., two or more vertebral levels). In a two vertebral level spinal stabilization system, the spinal stabilization system can include three bone fastener assemblies. One bone fastener assembly can be positioned in each of the vertebrae to be stabilized. An elongated member can be coupled and secured to the three bone fastener assemblies. In some embodiments, a single two-level spinal stabilization system can be installed in a patient. Such a system can be referred to as a unilateral, two-level stabilization system or a two-level, three-point stabilization system. In some embodiments, two three-point spinal stabilization systems can be installed in a patient on opposite sides of a spine. Such a system can be referred to as a bilateral, two-level stabilization system or a two-level, six-point stabilization system.

In some embodiments, combination systems can be installed. For example, a two-point stabilization system can be installed on one side of a spine, and a three-point stabilization system can be installed on the opposite side of the spine. The composite system can be referred to a five-point stabilization system.

Minimally invasive procedures can reduce trauma to soft tissue surrounding vertebrae that are to be stabilized. Only a small opening can need to be made in a patient. For example, for a single-level stabilization procedure on one side of the spine, the surgical procedure can be performed through a 2 cm to 4 cm incision formed in the skin of the patient. In some embodiments, the incision can be above and substantially between the vertebrae to be stabilized. In some embodiments, the incision can be above and between the vertebrae to be stabilized. In some embodiments, the incision can be above and substantially halfway between the vertebrae to be stabilized. Dilators, a targeting needle, and/or a tissue wedge can be used to provide access to the vertebrae to be stabilized without the need to form an incision with a scalpel through muscle and other tissue between the vertebrae to be stabilized. A minimally invasive procedure can reduce an amount of post-operative pain felt by a patient as compared to invasive spinal stabilization procedures. A minimally invasive procedure can reduce recovery time for the patient as compared to invasive spinal procedures.

Components of spinal stabilization systems can be made of materials including, but not limited to, titanium, titanium alloys, stainless steel, ceramics, and/or polymers. Some components of a spinal stabilization system can be autoclaved and/or chemically sterilized. Components that can not be autoclaved and/or chemically sterilized can be made of sterile materials. Components made of sterile materials can be placed in working relation to other sterile components during assembly of a spinal stabilization system.

Spinal stabilization systems can be used to correct problems in lumbar, thoracic, and/or cervical portions of a spine. Various embodiments of a spinal stabilization system can be used from the C1 vertebra to the sacrum. For example, a spinal stabilization system can be implanted posterior to the spine to maintain distraction between adjacent vertebral bodies in a lumbar portion of the spine.

In accordance with an aspect of the invention; a bone fastener assembly is provided. The bone fastener assembly includes a bone fastener, and a collar. The collar has an upper portion with a slot to receive an elongated member, a lower portion having a socket formed therein and an opening with a predetermined shape in communication with the socket, and a first longitudinal axis extending through the upper and lower portions. The bone fastener has a head portion to be received in the socket, and a shank portion to be attached to a vertebrae. The head portion has a first cross-sectional shape in a plane generally perpendicular to a second longitudinal axis extending through the head and shank portions of the fastener. The head portion further includes a second cross-sectional shape in a plane angled relative to the second longitudinal axis. The first cross-sectional shape is configured to prohibit movement of the head portion through the opening in the collar and the second cross-sectional shape is configured to allow movement of the head portion through the opening.

For purpose of explanation and illustration, and not limitation, an exemplary embodiment of the bone fastener assembly is shown in the accompanying figures. For example, FIGS. 1-3 illustrate a bone fastener in accordance with the invention shown generally by reference character 100. As shown in FIG. 2, the fastener 100 generally includes a head portion 102, a shank portion 104 and a neck portion 106 disposed therebetween. Alternative anchor members, such as hooks are contemplated to be within the scope of the present invention.

FIGS. 4-7 illustrate a collar in accordance with the invention shown generally by reference character 200, having an upper portion 202 with a slot 208 for receiving an elongated member (not shown), and a lower portion 204 having socket 206 formed therein for receiving the head of the fastener. The lower portion 204 includes an opening of predetermined shape such a generally circular shape 210 and a relief 212 extending from the circular opening, as will be discussed in further detail below. A first longitudinal axis 214 extends between upper and lower portions and through the opening as shown in FIGS. 5 and 13F. Preferably, the opening 210 is oriented generally perpendicular to the first longitudinal axis 214. The relief extends upwardly and outwardly a distance into the lower portion 204 of the collar.

In accordance with a particular aspect of the present invention, the fastener has a second longitudinal axis 108, which extends through head portion 102 and shank portion 104 as embodied herein. Further, head portion 102 includes a first cross-sectional shape in a plane perpendicular to the second longitudinal axis 108, and a second cross-sectional shape in a plane angled relative to the second longitudinal axis.

In a preferred embodiment, the second cross-sectional plane is angled 45° to the second longitudinal axis 108, as shown in FIG. 2. For example, the second cross-section is formed by machining a circular cut into the head 102 at a 45° angle to form facet 103, as illustrated in FIGS. 9-12D. Consequently, the diameter of the head 102 is smaller at the facet 103 than at spherical portion 105. Preferably, the second cross-sectional shape of the head, which coincides with facet 103, has a cross dimension which is approximately 90% of the diameter of the first cross-sectional shape. In one embodiment, the first cross-sectional shape relates to a generally spherical surface having a diameter of approximately 0.320 inches, and the second cross-sectional shape relates to a generally non-spherical surface, such as a cylindrical shape having a diameter of approximately 0.285 inches.

In accordance with another aspect of the invention, the opening in the bottom of the collar 200 is configured to permit insertion of the fastener 100 only when the circular cut is aligned with the opening at a particular angle, as illustrated in FIGS. 8A-C. In other words, when the circular cut, or facet 103, is aligned with the circular opening 210, the larger diameter portion 105 of head 102 registers with the relief cut extension 212 to permit insertion of the fastener from the bottom of the collar. Therefore, the larger diameter portion 105 can serve as a key to ensure proper alignment of the fastener and collar. In a preferred embodiment, the circular opening 210 in the bottom of the collar has a diameter of approximately 0.285 inches, which correlates to the diameter of the second cross-sectional shape formed by facet 103.

In accordance with another aspect of the invention, upon insertion of the fastener 100 into the collar such that the head 102 is received in the socket 206, the fastener can be rotated so that the second cross-sectional shape is no longer aligned with the opening. Accordingly, the fastener head 102 is received by the socket and prohibited from moving through the opening. For example, the fastener can be rotated 45° to ensure that the larger diameter portion 105 of the head or key, is displaced from the relief 212 and the smaller diameter facet is displaced from the circular portion of the opening. The fastener can be rotated relative to the second longitudinal axis extending through the fastener member. Alternatively, the fastener can be rotated relative to the plane of the opening in the collar.

Although reference is made to the opening having a circular portion and a relief and the second cross-sectional shape having a circular facet and key, alternative corresponding shapes are contemplated to be within the scope of the present invention.

A bone fastener can be, but is not limited to, a bone screw, a ring shank fastener, a barb, a nail, a brad, or a trocar. Bone fasteners and/or bone fastener assemblies can be provided in various lengths in an instrumentation set to accommodate variability in vertebral bodies. For example, an instrumentation set for stabilizing vertebrae in a lumbar region of the spine can include bone fastener assemblies with lengths ranging from about 30 mm to about 75 mm in 5 mm increments. A bone fastener assembly can be stamped with indicia (i.e., printing on a side of the collar). In some embodiments, a bone fastener assembly or a bone fastener can be color-coded to indicate a length of the bone fastener. In certain embodiments, a bone fastener with a 30 mm thread length can have a magenta color, a bone fastener with a 35 mm thread length can have an orange color, and a bone fastener with a 55 mm thread length can have a blue color. Other colors can be used as desired.

Figure 12C:
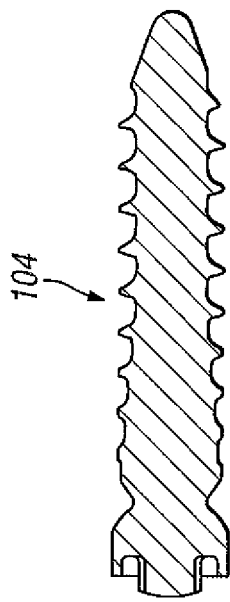
FIG. 12C is a cross-sectional view taken along line C-C in FIG. 12A.
Figure 12E:
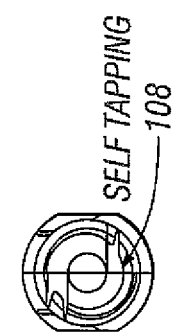
FIG. 12E is a bottom view of the fastener shown in FIG. 12A.
Figure 12A:
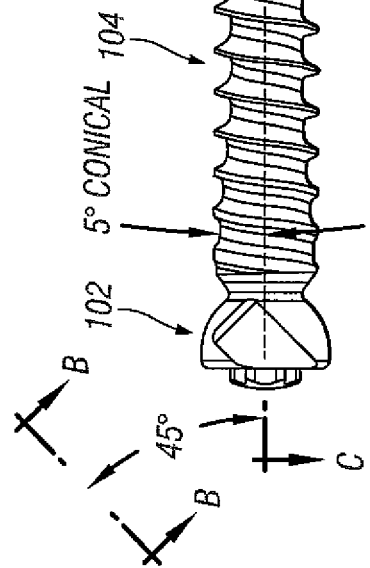
FIG. 12A is another front view of the fastener in accordance with the invention.
Figure 12B:
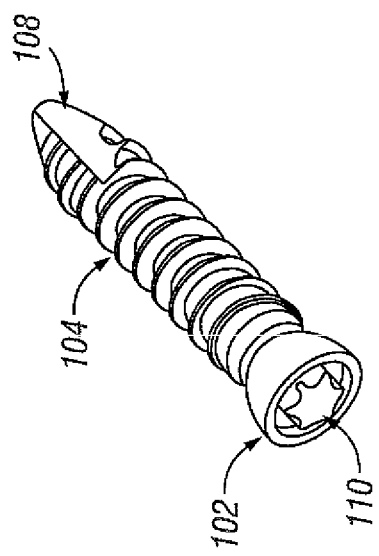
FIG. 12B is a perspective view taken along line B-B in FIG. 12A.
Figure 12D:
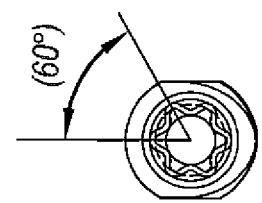
FIG. 12D is a top view of the fastener shown in FIG. 12A.

FIGS. 1-3, and 8-12E depict an embodiment of bone fastener 100 wherein the shank 104 includes thread. In some embodiments, the threads can include self-tapping start 108, as best shown in FIG. 12E. Self-tapping start 108 can facilitate insertion of bone fastener 108 into vertebral bone. Each bone fastener provided in an instrumentation set can have substantially the same thread profile and thread pitch. In an embodiment, the thread can have about a 4 mm major diameter and about a 2.5 mm minor diameter with a cancerous thread profile. In certain embodiments, the minor diameter of the thread can be in a range from about 1.5 mm to about 4 mm or larger. In certain embodiments, the major diameter of the thread can be in a range from about 3.5 mm to about 6.5 mm or larger. Bone fasteners with other thread dimensions and/or thread profiles can also be used. A thread profile of the bone fasteners can allow bone purchase to be maximized when the bone fastener is positioned in vertebral bone.

Figure 9:
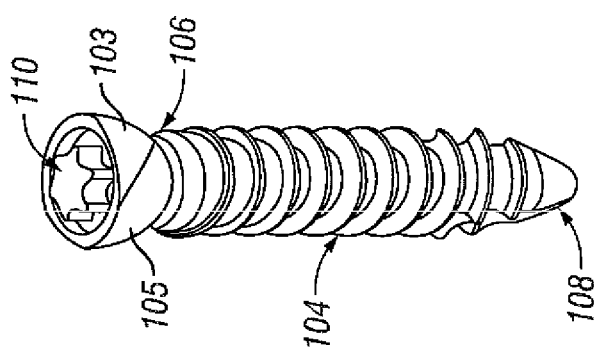
FIG. 9 is a perspective view of a representative embodiment of a fastener in accordance with the invention.

Head portion 102 of bone fastener 100 can include various configurations to engage a driver that inserts the bone fastener into a vertebra. In some embodiments, the driver can also be used to remove an installed bone fastener from a vertebra. In some embodiments, head 100 can include one or more tool portions 110, as shown in FIG. 9. Tool portions 110 can be recesses and/or protrusions designed to engage a portion of the driver. In some embodiments, bone fastener 100 can be cannulated for use in a minimally invasive procedure.

Neck 106 of bone fastener 100 can have a smaller diameter than adjacent portions of head 102 and shank 104. The diameter of neck 106 can fix the maximum angle that the collar of the bone fastener assembly can be rotated relative to bone fastener 100. In some embodiments, neck 106 can be sized to allow up to about 40° or more of angulation of the collar relative to the bone fastener. In some embodiments, the neck can be sized to allow up to about 30° of angulation of the collar relative to the bone fastener. In some embodiments, the neck can be sized to allow up to about 20° of angulation of the collar relative to the bone fastener.

The outer surface of the head 102 can have a smooth finish. In some embodiments, the outer surface can be surface treated, such as heavy grit blasting, or include coatings and/or coverings. Surface treatments, coatings, and/or coverings can be used to adjust frictional and/or wear properties of the outer surface of the head. In some embodiments, a portion of the outer surface of the head can be shaped and/or textured to limit a range of motion of the fastener relative to a collar of a bone fastener assembly.

As discussed above, spinal stabilization systems can include bone fastener assemblies having bone fasteners 100, collars 200, elongated member (not shown), and/or closure members (not shown). Other spinal stabilization system embodiments can include, but are not limited to, plates, dumbbell-shaped members, and/or transverse connectors.

As used herein, the term "collar" includes any element that wholly or partially encloses or receives one or more other elements. A collar can enclose or receive elements including, but not limited to, a bone fastener, a closure member, and/or an elongated member. A collar can have any of various physical forms. In some embodiments, a collar can have a "U" shape, however it is to be understood that a collar can also have other shapes. A collar can be open or closed. A collar having a slot and an open top, such as collar 200 shown in FIGS. 4-7 and 13A-F, can be referred to as an "open collar". A bone fastener assembly that includes an open collar can be referred to as an "open fastener". In some embodiments, an elongated member (not shown) can be top loaded into the open fastener. A closure member (not shown) can be coupled to the collar to secure the elongated member to the open fastener.

Alternatively, a collar that does not include a slot and an open top can be referred to as a "closed collar". A spinal implant that includes a closed collar can be referred to as a "closed implant". A closed collar can include an aperture, bore, or other feature in side surfaces for accommodating other components of a stabilization system (e.g., an elongated member). A set screw can be used to securely couple an elongated member to a closed implant.

In a preferred embodiment of the invention, collar 200 includes a body portion and arms 216. Arms 216 can extend from the lower body portion 204 as shown in FIGS. 4-5 and 13F. Body portion 204 of collar 200 can be greater in width than a width across arms 216 of collar 200 (i.e., body 204 can have a maximum effective outer diameter greater than a maximum effective outer diameter of arms 216). A reduced width across arms 216 allows a detachable member to be coupled to the arms without substantially increasing a maximum effective outer diameter along a length of collar 200. Thus, a reduced width across arms 216 can reduce bulk at a surgical site.

A height of body 204 can range from about 3 millimeters (mm) to about 7 mm. In an embodiment, a height of body 204 is about 5 mm. In a preferred embodiment the inner surface of collar 200 which defines the socket 206 can be machined to complement a portion of an outer surface of the fastener 100 that is to be positioned in collar 200. Machining of socket 206 can enhance retention of the fastener in the collar 200. Additionally, socket 206 can be complementary in shape to a portion of outer surface of fastener head 102 (see FIG. 5) so that the fastener is able to swivel in the collar. Inner surfaces and/or outer surfaces of collar 200 can be surface treated or include coatings and/or coverings to modify frictional properties or other properties of the collar.

A portion of the collar, and preferably the arms, can include a thread to receive a corresponding closure member. In a preferred embodiment, inner surfaces of arms 216 can include modified thread 218. Modified threads 218 can engage complementary modified threads of a closure member (not shown) to secure an elongated member (not shown) to a bone fastener assembly. Modified threads 218 can have a constant pitch or a variable pitch, as disclosed in U.S. Patent Application Publication No. 2006/0084993.

A height and a width of arms 216 can be sized as needed, for example, arms 216 can range in height from about 8 mm to about 15 mm. In an embodiment, a height of arms 216 is about 11 mm. A width (i.e., effective diameter) of arms 216 can range from about 5 mm to 14 mm. Arms 216 and body 204 form slot 208 which can be sized to receive an elongated member. Slot 208 can include, but is not limited to, an elongated opening of constant width, an elongated opening of variable width, a rectangular opening, a trapezoidal opening, a circular opening, a square opening, an ovoid opening, an egg-shaped opening, a tapered opening, and combinations and/or portions thereof. In some embodiments, a first portion of slot 208 can have different dimensions than a second portion of slot 208. In certain embodiments, a portion of slot 208 in first arm 216 can have different dimensions than a portion of slot 208 in second arm 216. When an elongated member is positioned in slot 208, a portion of the elongated member can contact a head of a bone fastener positioned in the collar.

In an embodiment of a collar, arms 216 of collar 200 can include one ore more openings and/or indentions 220, as shown in FIGS. 6 and 13A. Indentions 220 can vary in size and shape (e.g., circular, triangular, rectangular). Indentions 220 can be position markers and/or force application regions for instruments that perform reduction, compression, or distraction of adjacent vertebrae. In some embodiments, openings and/or indentions can be positioned in the body of the collar.

In accordance with a preferred embodiment, the bone fastener is rotatably positioned in a collar such that the bone fastener is able to move radially and/or rotationally relative to the collar (or the collar relative to the bone fastener) within a defined range of motion. The range of motion can be provided within a plane, such as by a hinged connection, or within a three-dimensional region, such as by a ball and socket connection. Motion of the bone fastener relative to the collar (or the collar relative to the bone fastener) is referred to as "angulation" and/or "polyaxial movement".

Preferably, a closure member (not shown) is coupled to a collar of a bone fastener assembly to fix an elongated member (not shown) positioned in the collar to the bone fastener assembly. In some embodiments, a closure member can be cannulated. In certain embodiments, a closure member can have a solid central core. A closure member with a solid central core can allow more contact area between the closure member and a driver used to couple the closure member to the collar. A closure member with a solid central core can provide a more secure connection to an elongated member than a cannulated closure member by providing contact against the elongated member at a central portion of the closure member as well as near an edge of the closure member.

A bottom surface of a closure member preferably includes structure and/or texturing that promotes contact between the closure member and an elongated member. A portion of the structure and/or texturing can enter and/or deform an elongated member when the closure member is coupled to the elongated member. Having a portion of the closure member enter and/or deform the elongated member can couple the elongated member to the closure member and a bone fastener assembly so that movement of the elongated member relative to the bone fastener assembly is inhibited.

The closure member can couple to collar 200 by a variety of systems including, but not limited to, standard threads, modified threads, reverse angle threads, buttress threads, or helical flanges. A buttress thread on a closure member can include a rearward-facing surface that is substantially perpendicular to the axis of the closure member. Additionally, closure member can be advanced into an opening in a collar to engage a portion of elongated member. In some embodiments, the closure member can inhibit movement of elongated member relative to collar 200.

Figure 13G:
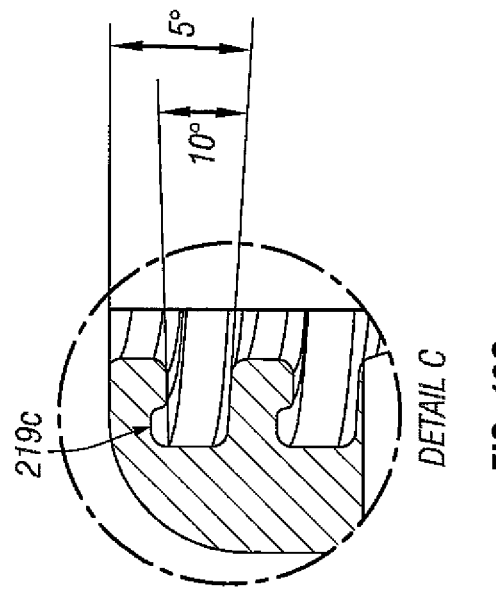
FIG. 13G is an enlarged view of section C in FIG. 13F.
Figure 13F:
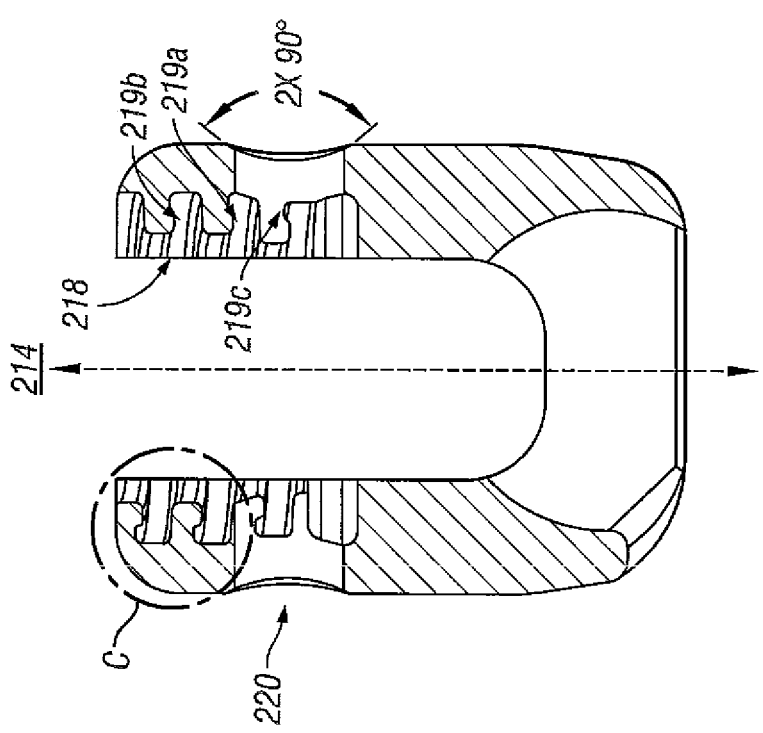
FIG. 13F is a cross-sectional view taken along line B-B in FIG. 13E.

FIGS. 5 and 13F-G depict a cross-sectional view of collar 200 having a female modified thread configured to receive a male modified thread (not shown) of a closure member. Male modified thread includes male distal surface and male proximal surface. Collar 200 includes female modified thread 218 on an inside surface of arms 216. Female modified thread 218 includes female proximal surface 219a and female distal surface 219b. Male proximal surface can couple to female distal surface 219a during use. Male proximal surface and female distal surface 219b can be load-bearing surfaces. A load can result from an upward load on the closure member, such as a load resulting when the elongated member positioned in a slot 208 of collar 200 is secured to the bone fastener assembly by the closure member.

Raised portions can be included on the male distal surface, and corresponding recessed portions 219c can be included on female proximal surface 219a. Cooperating surfaces of modified threads 218 can contact or be proximate to one another during use. As used herein, "proximate" means near to or closer to one portion of a component than another portion of a component. Engagement of cooperating surfaces of modified threads 218 during use can inhibit radial expansion of collar 200. Engagement of cooperating surfaces can inhibit spreading of arms 216 away from each other (i.e., inhibit separation of the arms). In some embodiments, cooperating surfaces can be substantially parallel to a central axis of the closure member. In other embodiments, cooperating surfaces can be angled relative to a central axis of the closure member.

In an embodiment, a bone fastener assembly and a closure member can be coupled with a running fit. A running fit (i.e., a fit in which parts are free to rotate) can result in predictable loading characteristics of a coupling of a bone fastener assembly and a closure member. Predictable loading characteristics can facilitate use of a closure member with a break-off portion designed to shear off at a predetermined torque. A running fit can also facilitate removal and replacement of closure members. In some embodiments, a closure member can include an interference fit (e.g., crest-to-root radial interference).

Various instruments can be used in a minimally invasive procedure to form a spinal stabilization system in a patient. Further description of these tools and the accompanying methods for performing the minimally invasive procedure are disclosed in U.S. patent application Ser. No. 10/697,793 filed Oct. 30, 2003 and now U.S. Pat. No. 7,250,052; Ser. No. 11/284,282 filed Nov. 21, 2005; and Ser. No. 11/337,863 filed Jan. 23, 2006; the entire disclosures of each are hereby incorporated by reference.

Figure 14:
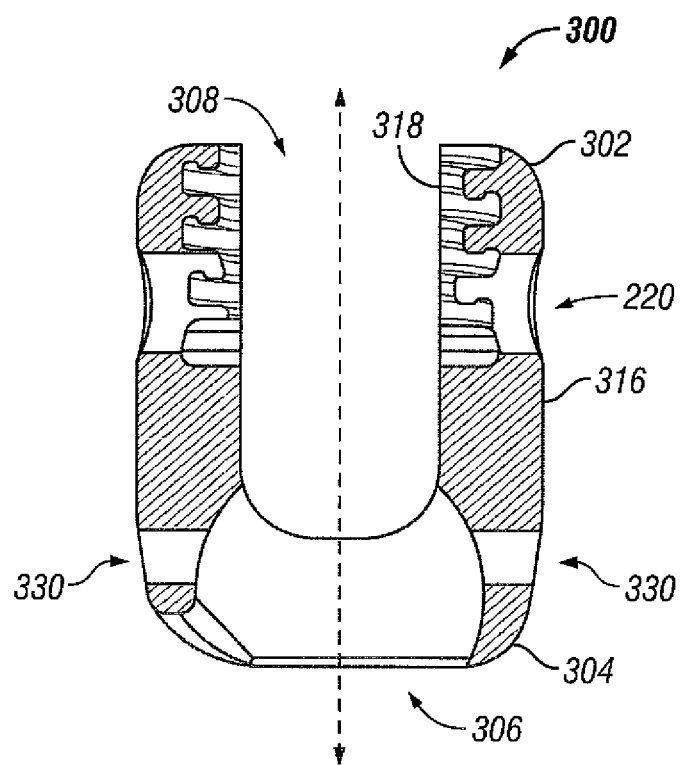
FIG. 14 is a cross-sectional view of one embodiment of a collar.
Figure 15:
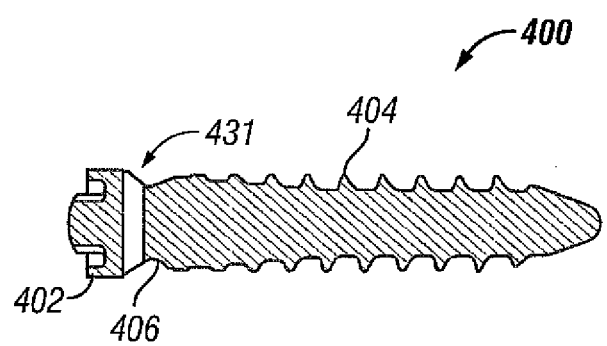
FIG. 15 is a cross-sectional view of one embodiment of a fastener.

With reference now to FIG. 14, FIG. 14 depicts one embodiment of a collar 300. Collar 300 can include upper portion 302, lower portion 304, socket 306, slot 308, arms 316, and threads 318. Lower portion 304 can define one or more apertures 330 extending through the side wall of lower portion 304 to socket 306. Apertures 330 can be created by drilling a hole through the side walls of lower portion 304 of socket 306. Collar 300 can include indentions 220 for engaging with instruments that perform reduction, compression, or distraction of adjacent vertebrae. FIG. 15 depicts one embodiment of a fastener 400 which can be used in conjunction with collar 300 to fasten elongated members to boney structures such as spinal vertebrae.

Fastener 400 can include head portion 402, shank portion 404, and neck portion 406. More particularly, Head portion 402 of fastener 400 can be generally spherical in shape, can be generally hemispherical in shape (with the hemispherical portion adjacent to neck portion 406), or can be otherwise, shaped, dimensioned, etc. to generally correspond to socket 306 of collar 300. Thus, head portion 402 of fastener 400 can be registered with socket 306 and inserted therein. Head portion 402 of fastener 400 can define aperture 431. Aperture 431 can be sized, shape, dimensioned, etc. to correspond to aperture 330 of collar 300 and can be created by drilling through head portion 402 of fastener 400. Aperture 431 of fastener 400 can be positioned to align with aperture 330 when head portion 402 of fastener 400 is in socket 306 of collar 300.

Figure 16:
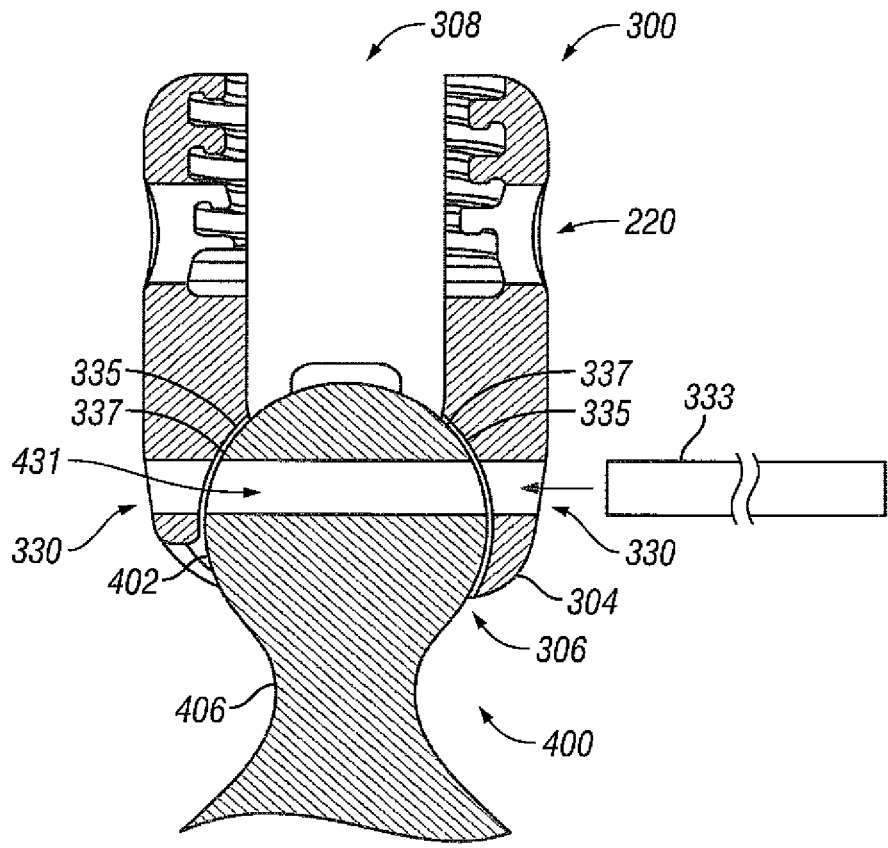
FIG. 16 is a cross-sectional view of one embodiment of a fastener and a collar.

FIG. 16 illustrates collar 300, fastener 400, and pin 333. FIG. 16 illustrates head portion 402 of fastener 400 inserted in socket 306 of lower portion 304. Aperture 431 of fastener 400 is illustrated as being aligned with apertures 330 of collar 300. Pin 333 and apertures 330 and 431 of collar 300 and fastener 400, respectively, can be shaped, dimensioned, etc. to correspond with each other. Pin 333 can be inserted through aperture 330 of collar 300 and into aperture 431 of fastener 400, thereby coupling fastener 400 to collar 300. Pin 333 can allow fastener 400 to angulate relative to collar 300 about an axis parallel to the longitudinal direction of pin 333. Pin 333 can fix fastener 400 relative to collar 300 to prevent angulation about axes of rotation other than the longitudinal axis of pin 333. Pin 333 can fix fastener 400 relative to collar 300 against movement in a direction between socket 306 and slot 308. Lower portion 304 of collar 300 can prevent fastener 400 from translating in directions defined by the walls of socket 306. Thus, pin 333 and lower portion 304 of collar 300 can allow fastener 400 to angulate about pin 333 within a selected plane while preventing other movements of fastener 400 relative to collar 300. Neck portion 406 of fastener 400 and lower portion 304 of collar 300 can be configured to limit angulation of fastener 400 to a defined range of motion.

In use, loads on collar 300 and fastener 400 can be born by collar 300, fastener 400, and pin 333 in various ways. For instance, the shape, dimensions, etc. of socket 306 of collar 300 can define bearing surface 335 toward the interior end of socket 306 whereas head portion 402 of fastener 400 can define bearing surface 337. Bearing surface 337 can correspond in location, shape, dimensions, etc. to bearing surface 335 of collar 300. Bearing surfaces 335 and 337 can be made of materials sufficiently hard so as to bear loads transmitted between collar 300 and fastener 400 without damage to bearing surfaces 335 and 337. In some embodiments, the shape, dimensions, etc. of socket 306 of collar 300 and fastener 400 can allow pin 333 to carry some or all of various loads transmitted between collar 300 and fastener 400. Collar 300 can include indentions 220 for engaging with instruments that perform reduction, compression, or distraction of adjacent vertebrae.

Figure 17:
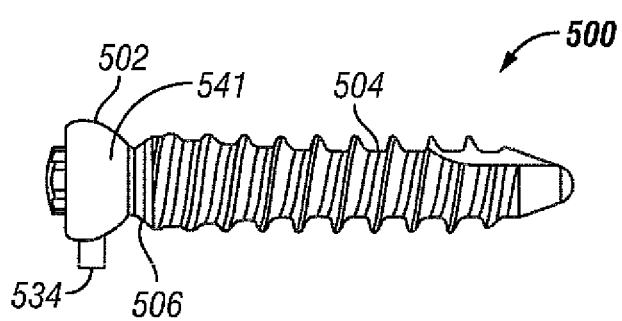
FIG. 17 is a side elevation view of one embodiment of a fastener.

With reference now to FIG. 17, FIG. 17 illustrates one embodiment of a fastener 500 including head portion 502, shank portion 504, and neck portion 506. Head portion 502 can include one, or more, pins 534 extending radially from head portion 502. Pin 534 can be configured to correspond with aperture 330 of collar 300 so that pin 534 can allow fastener 500 to angulate about pin 534. Pin 534 and the walls of socket 306 can be configured to prevent other movements of fastener 500 relative to collar 300.

Head portion 502 and socket 306 can be configured to allow head portion 502 with pin 534 thereon to be inserted into socket 306. For instance, side 541 of fastener 500 can be flat or semi-spherical to allow head portion 502 of fastener 500 (including pin 534) to be inserted into socket 306 of collar 300. More particularly, head portion 502 of fastener 500 and socket 306 of collar 300 can be configured so that head portion 502 can be registered with socket 306. Head portion 502 of fastener 500 can be oriented with respect to socket 306 so that pin 534 generally points toward aperture 330. Fastener 500 can be translated toward collar 300 so that head portion 502 of fastener 500 is inserted into socket 306 with pin 534 of head portion 502 clearing the walls of socket 306. Fastener 500 can then be rotated relative to collar 300 to bring pin 534 into engagement with aperture 330 of collar 300. Fastener 500 can be rotated further with respect to collar 300 to insert pin 534 of fastener 500 into aperture 330 of collar 300.

When fastener 500 is set in a particular boney structure (such as a vertebra), or at other times, collar 300 can be placed adjacent to head portion 502 of fastener 500 with socket 306 and head portion 502 registering with each other and with aperture 330 of collar 300 and pin 534 of fastener 500 generally aligned with each other. Collar 300 can be rotated with respect to fastener 500 to allow socket 306 to be translated to a position at which socket 306 partially encloses head portion 502 (including pin 534). Collar 300 can then be rotated to engage pin 534 of fastener 500 with aperture 330 of collar 300. Collar 300 can be further rotated to insert pin 534 of fastener 500 into aperture 330 of collar 300. An elongated member can then be anchored to the boney structure by placing it in slot 308 and inserting a closure member into slot 308.

Figure 18:
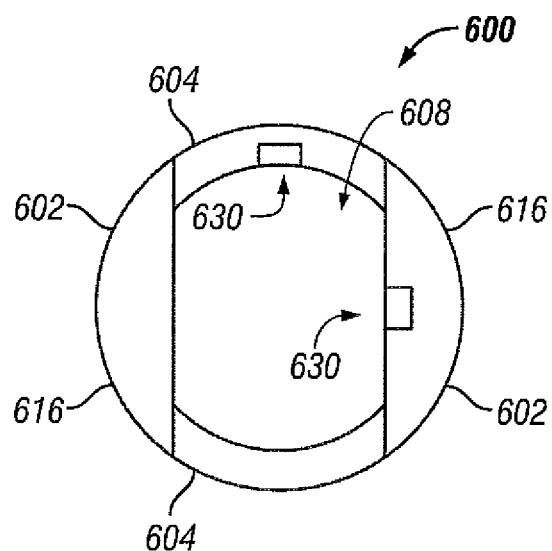
FIG. 18 is a top plan view of one embodiment of a collar.
Figure 19:
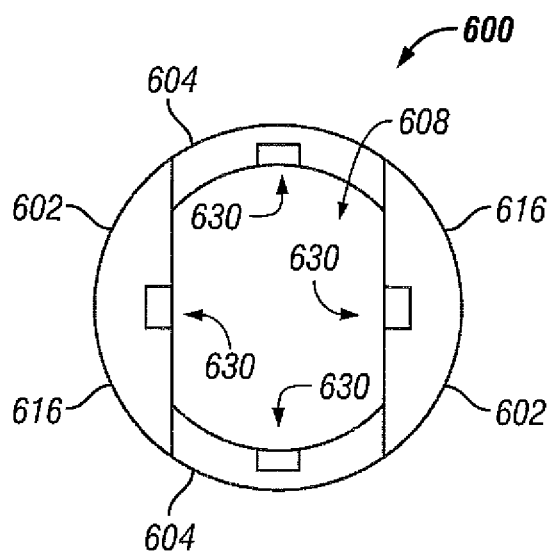
FIG. 19 is a top plan view of one embodiment of a collar.

FIGS. 18 and 19 depict top views of some embodiments of collars 600. In some embodiments, collar 600 can have two, three, four, or more apertures 630 whereas fastener 500 (see FIG. 17) can include a corresponding number of pins 534. In some embodiments, socket 306 can define one or more reliefs corresponding to pins 534 of fastener 500 to allow head portion 502 to be translated to a location where pins 534 can engage apertures 630. In some embodiments, socket 306 can define a race to allow head portion 502 (with pins 534) to be rotated within socket 306 to bring pins 534 into alignment with apertures 630. Apertures 630 can extend partially or completely through the side walls of lower portion 604. Apertures 630 can extend in a direction from slot 608 into upper portions 602 and in a direction from slot 608 into lower portions 604 of collar 600. Apertures 630 can extend along slot 608 from lower portions 604 to the proximal ends of arms 616 and lower portion 602.

Figure 20:
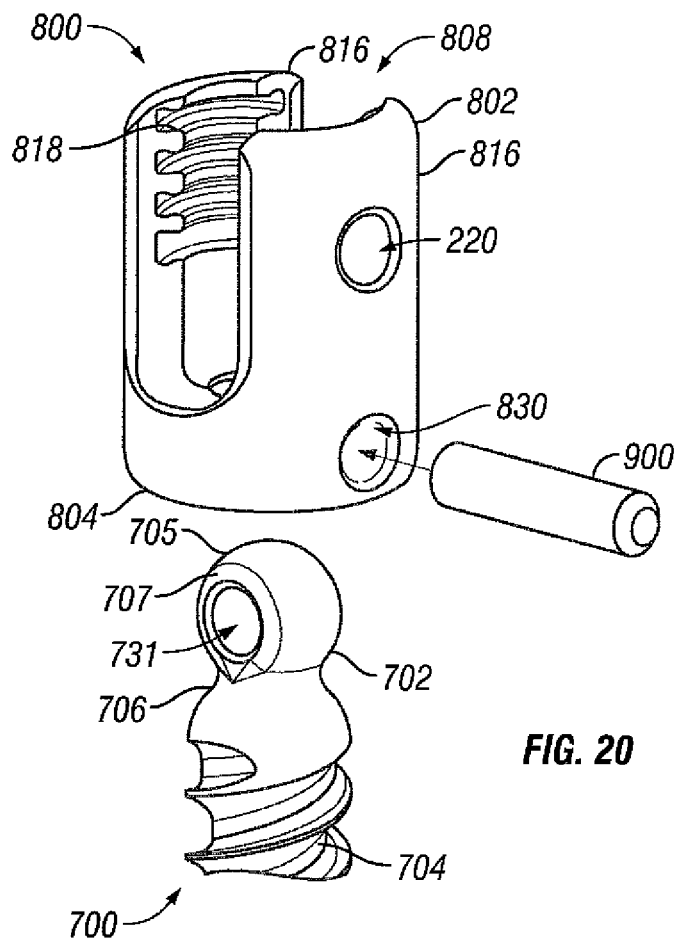
FIG. 20 is a perspective view of one embodiment of a fastener assembly.
Figure 21:
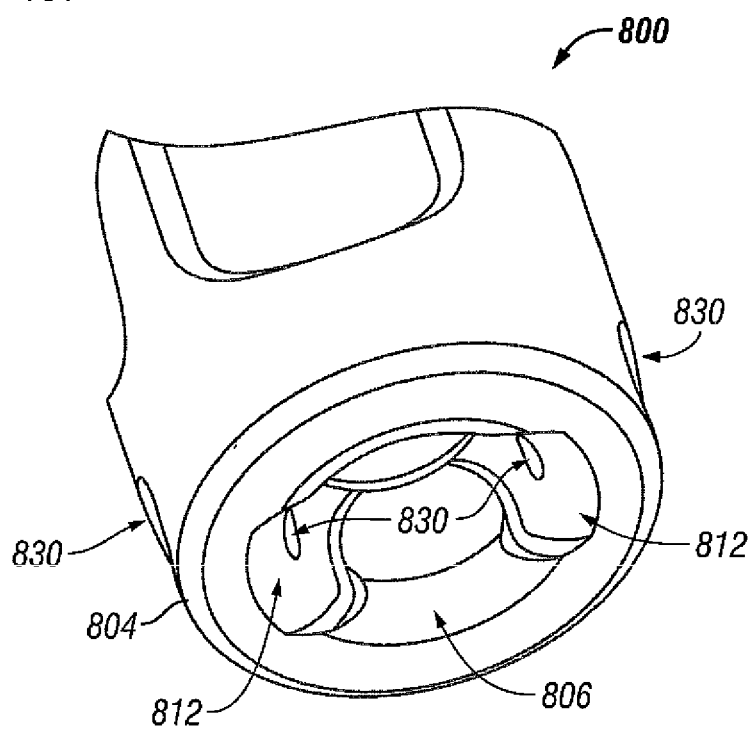
FIG. 21 is a perspective view of one embodiment of a collar.

With regard to FIG. 20, one embodiment of a fastener 700, a collar 800, and a pin 900 is depicted. Fastener 700 can include head portion 702, shank portion 704, and neck portion 706. Head portion 702 of fastener 700 can include a semi-spherical portion 705 with a pair of flats 707 on opposite sides of semi-spherical portion 705. Head portion 702 can define aperture 731 for accepting pin 900. Collar 800 can include upper portion 802, lower portion 804, and arms 816. Collar 800 can define slot 808 with threads 818 for accepting an elongated member and apertures 830 for accepting pin 900. FIG. 21 illustrates lower portion 804 of collar 800 including socket 806, reliefs 812, and apertures 830. Flats 707 of fastener 700 (see FIG. 20) can register with reliefs 812 of collar 800 to allow head portion 702 of fastener 700 to translate into socket 806 of collar 800 to a location where aperture 731 of fastener 700 can align with apertures 830 of collar 800. Apertures 731 and 830 of fastener 700 and collar 800 respectively can be configured to correspond in size, shape, etc. with pin 900. Pin 900 can be inserted into apertures 731 and 830 of fastener 700 and collar 800, respectively, to allow fastener 700 to angulate relative to collar 800 within a selected plane while otherwise being fixed with respect to collar 800. Collar 800 can include indentions 220 for engaging with instruments that perform reduction, compression, or distraction of adjacent vertebrae.

Figure 22:
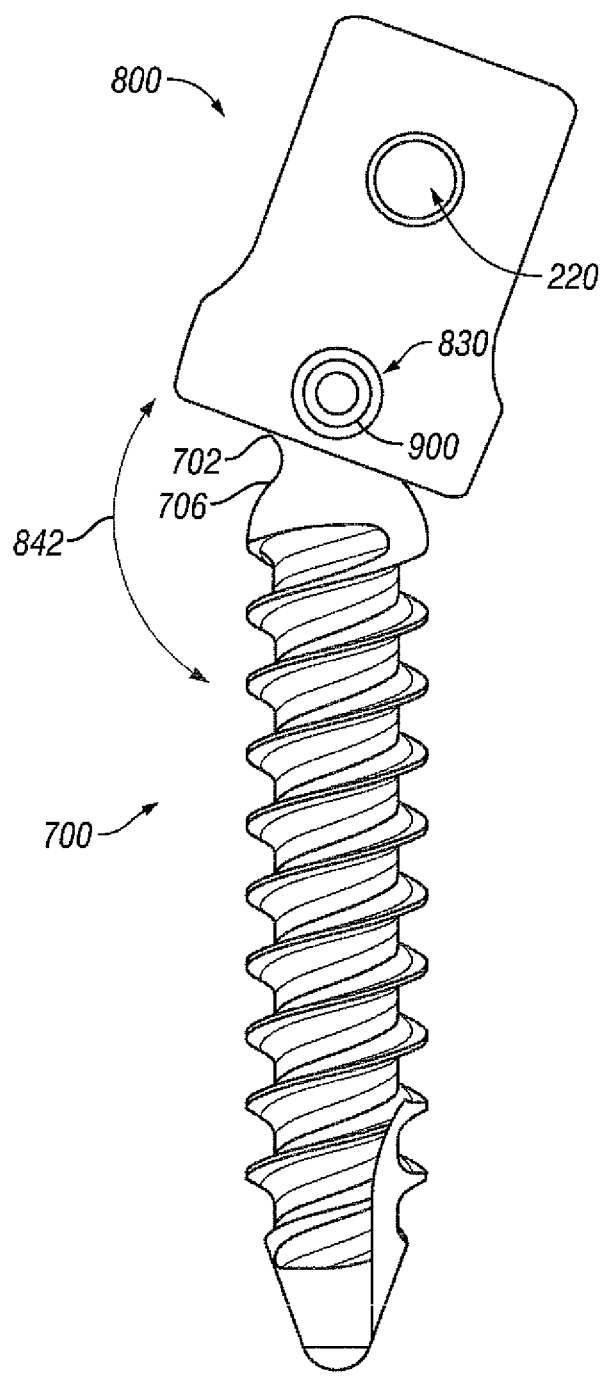
FIG. 22 is a side elevation view of a fastener assembly.

FIG. 22 depicts one embodiment of a fastener 700, a collar 800, and a pin 900. In FIG. 22, head portion 702 of fastener 700 is inserted in socket 806 (see FIG. 21) with neck and shank portions 706 and 704, respectively, extending from collar 800. Directional arrow 842 indicates that fastener 700 can angulate about pin 900 in apertures 830 and 731 (see FIG. 20) within a selected plane. Neck portion 706 of fastener 700 and lower portion 804 of collar 800 can be configured so that angulation of fastener 700 about pin 900 is limited to a defined range within the selected plane. Collar 300 can include indentions 220 for engaging with instruments that perform reduction, compression, or distraction of adjacent vertebrae.

In the foregoing specification, specific embodiments have been described with reference to the accompanying drawings. However, as one skilled in the art can appreciate, embodiments of the anisotropic spinal stabilization rod disclosed herein can be modified or otherwise implemented in many ways without departing from the spirit and scope of the disclosure. Accordingly, this description is to be construed as illustrative only and is for the purpose of teaching those skilled in the art the manner of making and using embodiments of an anisotropic spinal stabilization rod. It is to be understood that the embodiments shown and described herein are to be taken as exemplary. Equivalent elements or materials may be substituted for those illustrated and described herein. Moreover, certain features of the disclosure may be utilized independently of the use of other features, all as would be apparent to one skilled in the art after having the benefit of this description of the disclosure.

The invention claimed is:

1. A method for assembling a monoaxial bone fastener system from a polyaxial bone fastener system wherein the polyaxial bone fastener system includes a collar having an upper portion with a slot formed therein to receive an elongated member, a lower portion having a socket formed therein and an opening having a relief with a predetermined non-circular shape in communication with the socket, and a first longitudinal axis extending through the upper and lower portions of the collar, the polyaxial bone fastener system further including a fastener member having a head portion to be received in the socket of the lower portion of the collar, a shank portion to be attached to a vertebra, and a second longitudinal axis extending through the head portion and shank portion of the fastener member, the head portion of the fastener member having a non-circular cross-sectional shape in a plane generally perpendicular to the second longitudinal axis, wherein the non-circular cross-sectional shape of the head portion of the fastener member corresponds to the predetermined non-circular shape of the relief at the lower portion of the collar, the method comprising:

- aligning the collar with the fastener member with the non-circular cross-sectional shape of the head portion registering with the predetermined non-circular shape of the relief at the lower portion of the collar when the second longitudinal axis of the fastener member is angled with respect to the first longitudinal axis of the collar;
- inserting the entire head portion of the fastener member into the socket through the opening in the lower portion of the collar;
- rotating of the head portion of the fastener member in the socket of the collar to orient the non-circular cross-sectional shape of the head portion of the fastener member in juxtaposition with an inner surface of the socket of the collar to prohibit movement of the head portion through the opening at the lower portion of the collar; and
- angulating the fastener member polyaxially relative to the collar within a defined range of motion.

2. A bone fastener assembly comprising:

a collar having an upper portion with a slot formed therein to receive an elongated member, a lower portion having a socket formed therein and an opening having a relief with a predetermined non-circular shape in communication with the opening, and a first longitudinal axis extending through the upper and lower portions;

a fastener member having a head portion to be received in the socket, a shank portion to be attached to a vertebra, and a second longitudinal axis extending through the head portion and shank portion of the fastener member, the head portion of the fastener member having a spherical surface and a non-circular cross-sectional shape in a plane generally perpendicular to the second longitudinal axis;

the non-circular cross-sectional shape of the head portion of the fastener member being configured to correspond to the predetermined non-circular shape of the relief at the lower portion of the collar such that registration of the non-circular cross-sectional shape of the head portion of the fastener member with the predetermined non-circular shape of the relief at the lower portion of the collar occurs when the second longitudinal axis of the fastener member is angled with respect to the first longitudinal axis of the collar, thereby allowing movement of the entire head portion of the fastener member through the opening at the lower portion of the collar and wherein subsequent rotation of the head portion of the fastener member in the socket of the collar orients the non-circular cross-sectional shape of the head portion of the fastener member in juxtaposition with an inner surface of the socket of the collar to prohibit movement of the head portion of the fastener member through the opening of the collar and to allow angulation of the fastener member polyaxially relative to the collar within a defined range of motion.

* * * * *